Figure 1:
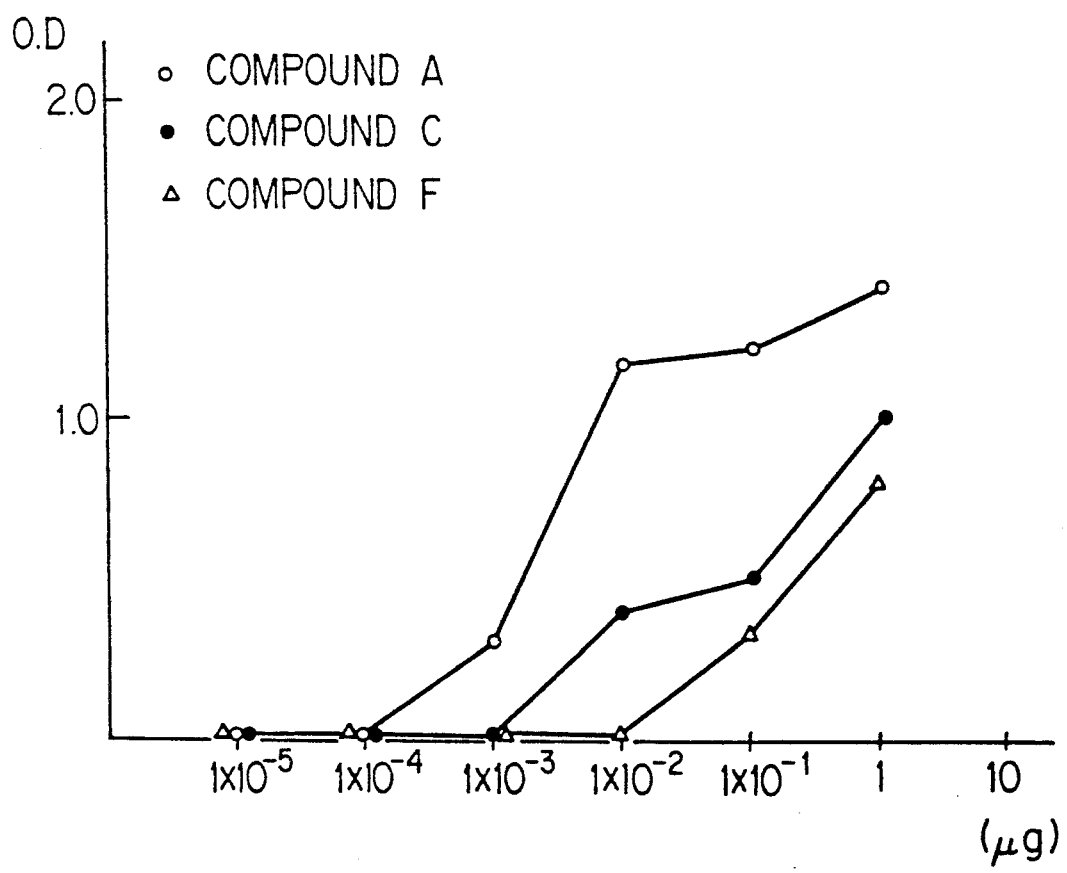

United States Patent [19]

Kawamura et al.

[11] Patent Number: 5,158,886
[45] Date of Patent: Oct. 27, 1992

[54] MONOCLONAL ANTIBODIES SPECIFIC FOR FREE N-ACETYLFURAMINIC ACID AND BETA-GLYCOSIDES AND BETA-GLYCOCONJUGATES THEREOF

[75] Inventors: Atsushi Kawamura; Isao Suda, both of Tokorozawa; Kinji Takada, Tokyo; Masayoshi Ito, Kunitachi; Yoshiyasu Shitori, Tokyo, all of Japan

[73] Assignee: MECT Corporation, Tokyo, Japan

[21] Appl. No.: 268,895

[22] Filed: Nov. 8, 1988

[30] Foreign Application Priority Data

Nov. 13, 1987 [JP] Japan ............................... 63-287119
Feb. 8, 1988 [JP] Japan ................................ 63-26848

[51] Int. Cl.$^5$ ...................... C12N 45/20; C12N 5/20; C07K 15/28; C12P 21/08
[52] U.S. Cl. ........................... 435/240.27; 530/388.9; 435/172.2; 435/70.21
[58] Field of Search ........................ 530/387, 388.9; 435/240.27, 172.2, 70.21

[56] References Cited

U.S. PATENT DOCUMENTS 4,694,076 9/1987 Ogawa et al.

OTHER PUBLICATIONS

The Journal of Biological Chemistry, vol. 262, No. 3, pp. 1358–1362, (1987), Katsuyoshi Shigeta et al.
Chapter 17 of Publication "Handbook of Experimental Immunology", vol. 4, pp. 117.1–117.20, (1986), Weir & Herzenberg.
Zeitschrift Fur Parasitenkunde, vol. 71, No. 5, 1985, pp. 663–672, Springer-Verlag, Berlin, DE; A. Bohn et al.: "Characterization of Antigens of the Nematode Nippostronylus Brasiliensis by Monoclonal Antibodies'- '*Abstract; p. 664, line 17–p. 665, line 22; p. 669, lines 7–12.
Proceedings of the National Academy of Sciences, vol. 76, No. 10, Oct. 1979, pp. 4913–4917, Washington, U.S.; G. S. Eisenbarth et al.; "Monoclonal Antibody to a Plasma Membrane Antigen of Neurons" * Abstract; pp. 4917, col. 1, lines 11–14.

*Primary Examiner*—John J. Doll
*Assistant Examiner*—Paula Hutzell
*Attorney, Agent, or Firm*—Oblon, Spivak, McClelland, Maier & Neustadt

[57] ABSTRACT

A hybridoma producing a monoclonal antibody specific for free N-acetylneuraminic acid or beta glycoconjugates thereof, is herein disclosed. The hybridoma can be generated by fusing (i) B cells of lymphocytes obtained by immunizing an animal with an N-acetylneuraminic acid or a beta-glycoconjugate thereof, and (ii) myeloma cells.

6 Claims, 4 Drawing Sheets

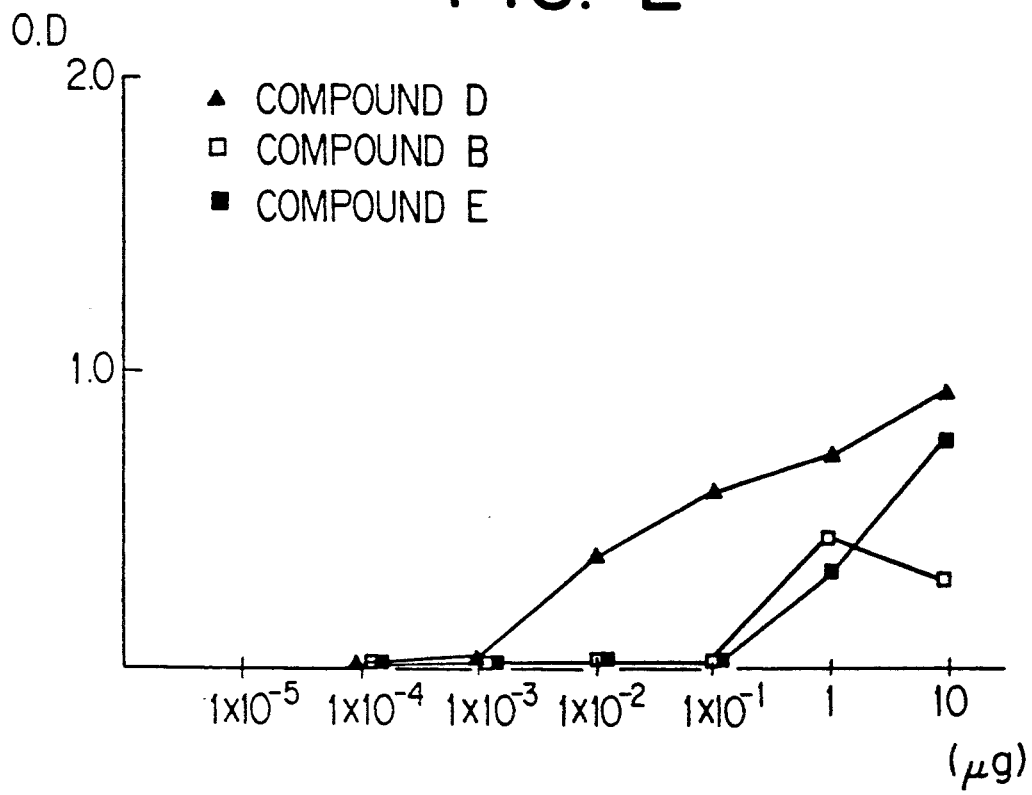
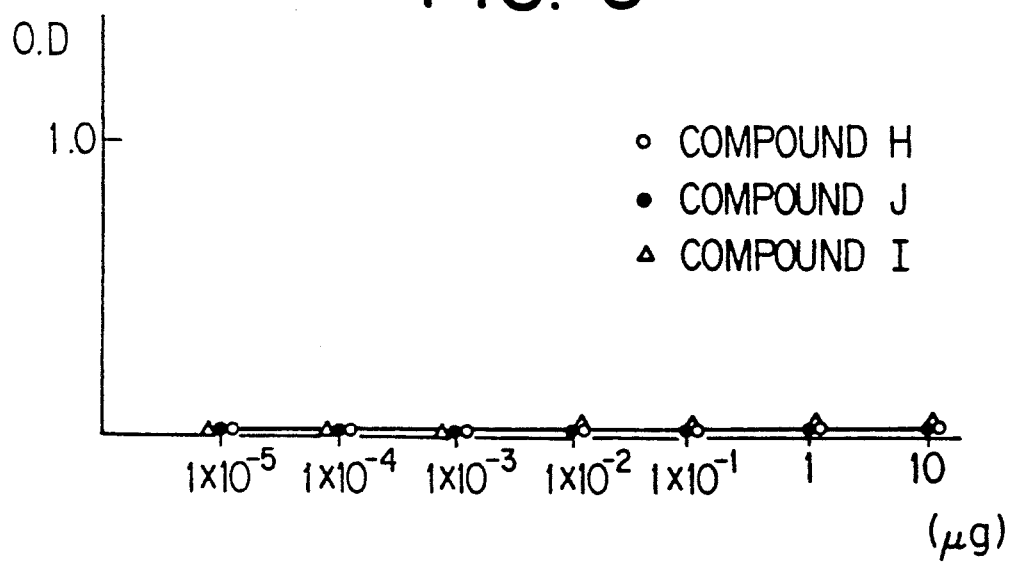

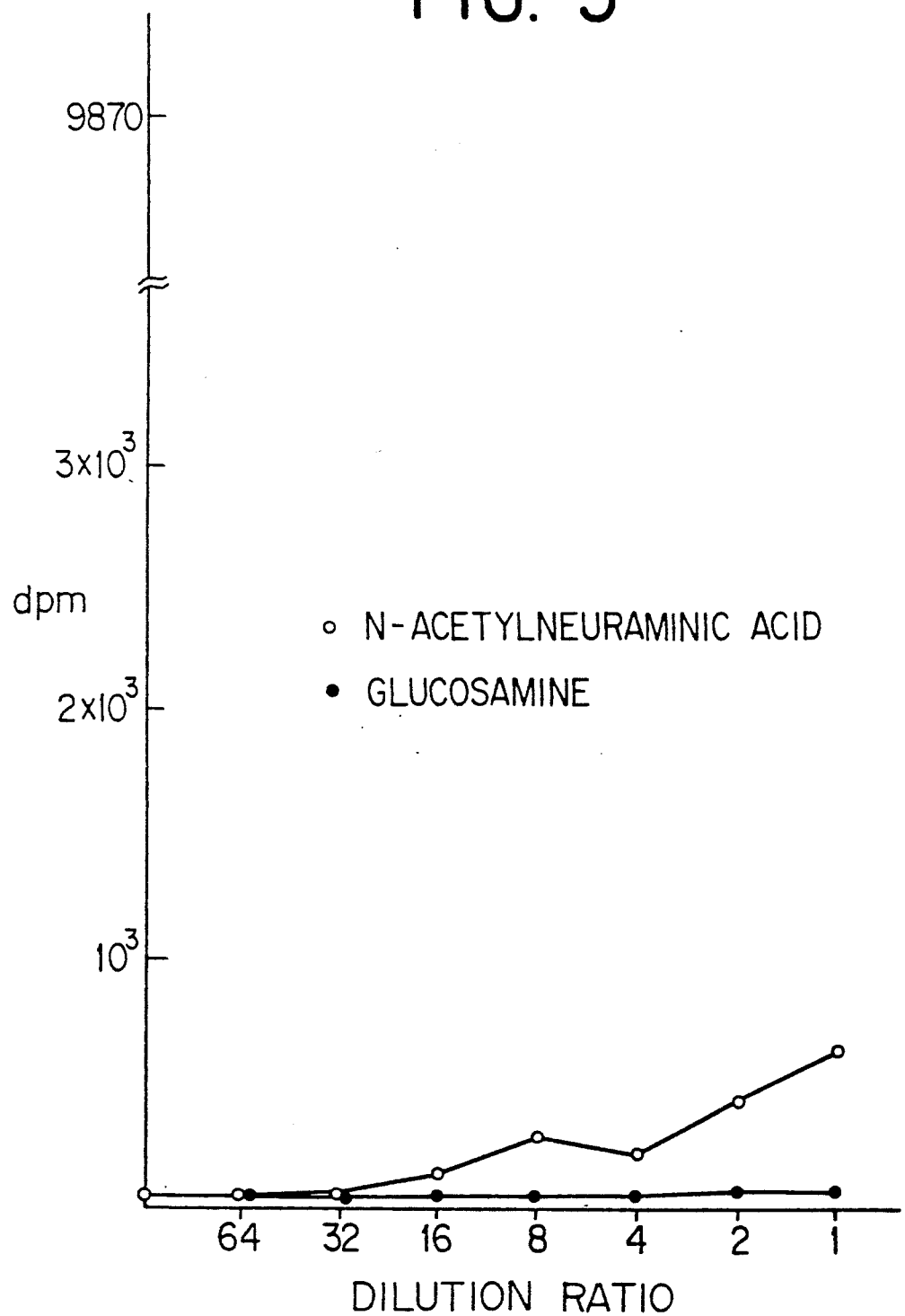

MONOCLONAL ANTIBODIES SPECIFIC FOR FREE N-ACETYLFURAMINIC ACID AND BETA-GLYCOSIDES AND BETA-GLYCOCONJUGATES THEREOF

BACKGROUND OF THE INVENTION

1. Field of the Invention

The present invention relates to a novel hybridoma, a method for generating the same and monoclonal antibodies specific to N-acetylneuraminic acid in the beta-arrangement, which are produced by the hybridoma.

2. Description of the Prior Art

In 1975, Kohler and Millstein developed a method for producing monoclonal antibodies utilizing a hybridoma which makes it possible to almost perpetually produce such an antibody having uniform specificity and other characteristics. Earlier than this, it has been recognized that ordinary anti-sera produced by immunizing an animal with an antigen inclusive of tumour cells contain a variety of antibodies differing in their specificity and characteristic properties. The method by Kohler et al. requires the fusion of spleen cells of an immunized animal with an immortal myeloma cell line and the screening of hybridomas generated by the cell fusion for desired antibody production, i.e., the selection of a clone which can produce or secrete an antibody having a desired specificity from fused cells referred to as "hybridoma" thus generated. Such a clone can continuously produce an antibody inherent thereto. The cloned hybridoma can perpetually be cultured and on the contrary, it can be stored in the frozen state in liquid nitrogen. Thus, the stable supply of individual antibodies can be ensured.

Antibodies are proteins capable of specifically recognizing other molecules or substances known as antigens and also capable of binding to the same. A monoclonal antibody is of course an antibody, but the characteristic properties thereof are quite uniform and it recognizes only one antigen or antigenic determinant. A variety of hybridomas are generated by cell fusion technique, but all of the cloned hybridomas formed by fusing, for instance, myeloma cells with antibody-producing cells derived from an immunized animal are not specific to a desired antigen. Moreover, since antibodies produced by different cloned hybridomas can react with different antigenic determinants on the same molecule, an antibody produced by a specific cloned hybridoma is different from those produced by other clones even if they are specific to a desired antigen. Therefore, it is impossible to correctly forecast the specific site of an antigen molecule which can be recognized by each individual monoclonal antibody. Nowadays, various techniques for producing monoclonal antibodies and those for generating hybridomas capable of producing the same are well known in the art. In this respect, reference can be made to a recent publication "Monoclonal Hybridoma Antibodies: Techniques and Applications", edited by John G. Hurrell, 1983.

It is known that N-acetylneuraminic acid is present at the terminus of a sugar chain of a glycoconjugate (complex carbohydrate) and plays various biologically important roles. It has recently been reported that the substantial increase in the content of free N-acetylneuraminic acid in the blood or urine is observed in patients suffering from malignant tumour or acute inflammatory diseases and thus the quantitative and/or qualitative measurement thereof has attracted special interest recently.

In other words, since the monoclonal antibody has high specificity to a specific antigen and thus detects the same in a high sensitivity, to apply such a monoclonal antibody to the diagnosis of cancer for the purposes of early diagnosis or early treatment thereof would be expected. The diagnosis would be realized by detecting N-acetylneuraminic acid present in, for instance, the serum of individual using a monoclonal antibody as a cancer marker, if such a monoclonal antibody specific to aforesaid free N-acetylneuraminic acid can be obtained.

Under such circumstances, there has been proposed a variety of methods for detecting or quantitatively determining the free N-acetylneuraminic acid in a high sensitivity. However, these methods conventionally established suffer from problems concerning simplicity and specificity to a desired antigen or antigenic determinant.

All the N-Acetylneuraminic acid residues present at the termini of sugar chains of naturally occurring complex carbohydrate are in the alpha-arrangement and on the contrary, the free N-acetylneuraminic acid is in the beta-arrangement. Among the monoclonal antibodies specific to these complex carbohydrates, there are obtained many monoclonal antibodies specifically recognizing sites which contain N-acetylneuraminic acid residues as the epitope, but for the above reasons every antibody does not have an ability of recognizing such free N-acetylneuraminic acid and ability of binding thereto. Moreover, N-acetylneuraminic acid is a hapten with a low molecular weight and thus it has only a low antigenicity. Therefore, it seems very difficult to obtain monoclonal antibodies even if an animal is immunized with such a low molecular weight hapten.

SUMMARY OF THE INVENTION

Accordingly, an object of the present invention is to provide a hybridoma capable of producing a monoclonal antibody having high immunospecificity to free N-acetylneuraminic acid residues present in the blood and/or urine of patients suffering from malignant tumour or acute inflammatory diseases in an elevated concentration.

Another object of the present invention is to provide a method for generating such a hybridoma capable of producing a monoclonal antibody specific to free N-acetylneuraminic acid (or the residue thereof).

A further object of the present invention is to provide a monoclonal antibody specific to the epitope carrying free N-acetylneuraminic acid residues.

The inventors of the present invention have performed various studies to eliminate the above problems accompanied by the conventional techniques and found that a monoclonal antibody specific to a desired epitope or antigenic determinant can be obtained by utilizing a chemically synthesized sialic acid derivative in the beta-arrangement as an immunogen. Thus the present invention has been completed on the basis of such a finding.

According to an aspect of the present invention, there is provided a novel hybridoma which produces a monoclonal antibody specific to N-acetylneuraminic acid or derivatives thereof in the beta-arrangement as an epitope or antigenic determinant.

According to another aspect of the present invention, there is provided a method for generating hybridoma which produces a monoclonal antibody specific to N-acetylneuraminic acid or a derivative thereof in the beta-arrangement as an epitope or antigenic determinant and the method comprises fusing (i) B cells or B lymphocytes obtained by immunizing an animal with a derivative of N-acetylneuraminic acid in the beta-arrangement as an antigen and (ii) myeloma cells.

According to a further aspect of the present invention, there is provided a monoclonal antibody having high specificity to N-acetylneuraminic acid in the beta-arrangement as an epitope or antigenic determinant.

BRIEF DESCRIPTION OF THE ACCOMPANYING DRAWINGS

Figure 4:
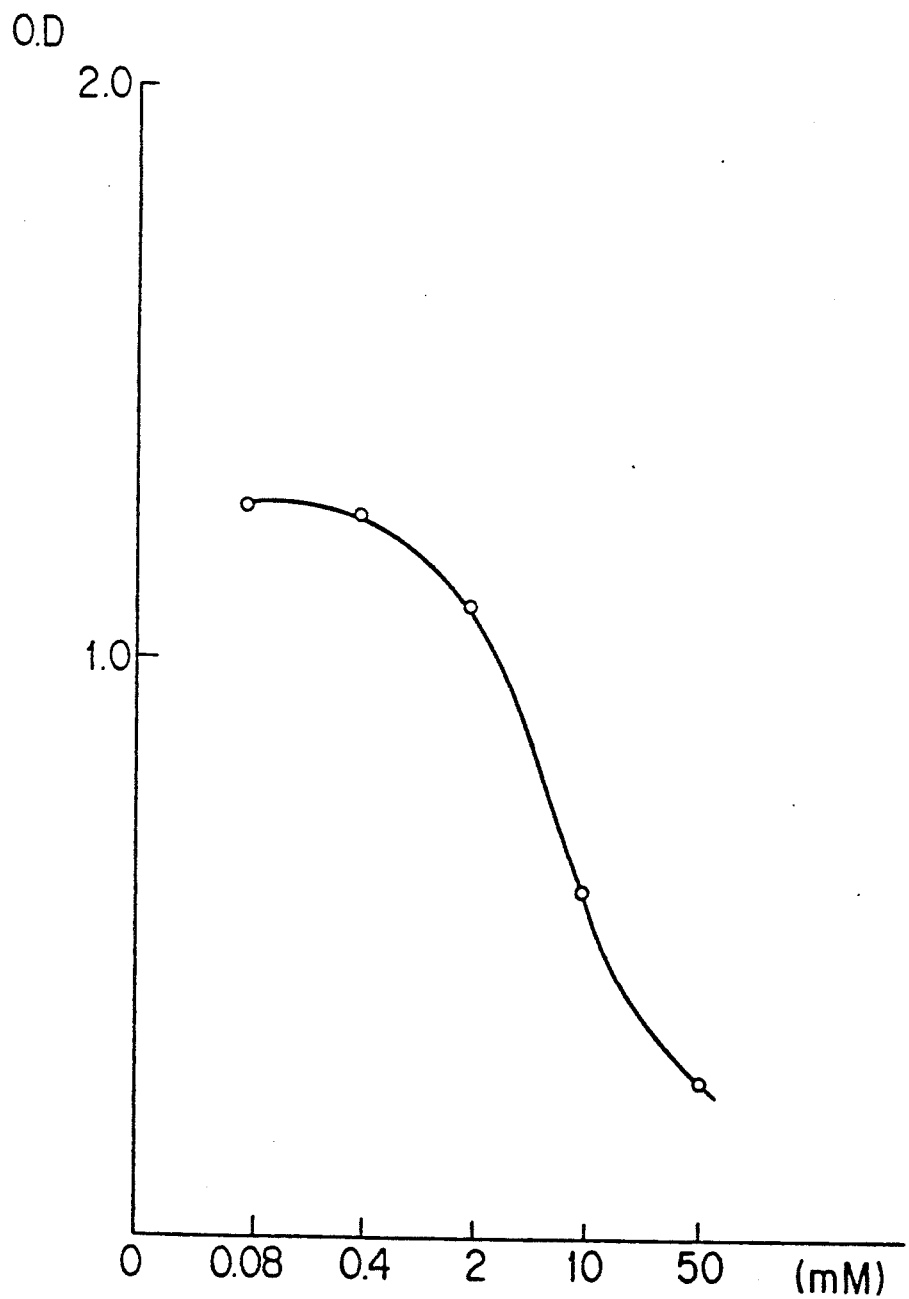

FIGS. 1 to 3 are diagrams illustrating the results of the cross reaction between the monoclonal antibody of this invention and various derivatives of N-acetylneuraminic acid in the beta-arrangement, obtained by enzyme-labeled antibody technique;

FIG. 4 is a diagram illustrating the competitive inhibitory effect of free N-acetylneuraminic acid on the binding of the monoclonal antibody of this invention and Compound (A) serving as an antigen, which is examined in accordance with enzyme-labeled antibody technique; and FIG. 5 shows the results of binding reaction between the monoclonal antibody and N-acetylneuraminic acid labeled with a radioisotope.

DETAILED EXPLANATION OF THE INVENTION

The present invention will hereunder be described in more detail.

The hybridoma of the present invention can be generated according to the aforesaid method by Kohlor et al. In other words, the hybridoma can be produced by fusing B cells derived from an animal which is immunized with an antigen and myeloma cells. In this respect, the "antigen" used herein is a derivative of N-acetylneuraminic acid in the beta-arrangement. Specific examples thereof are as follows:

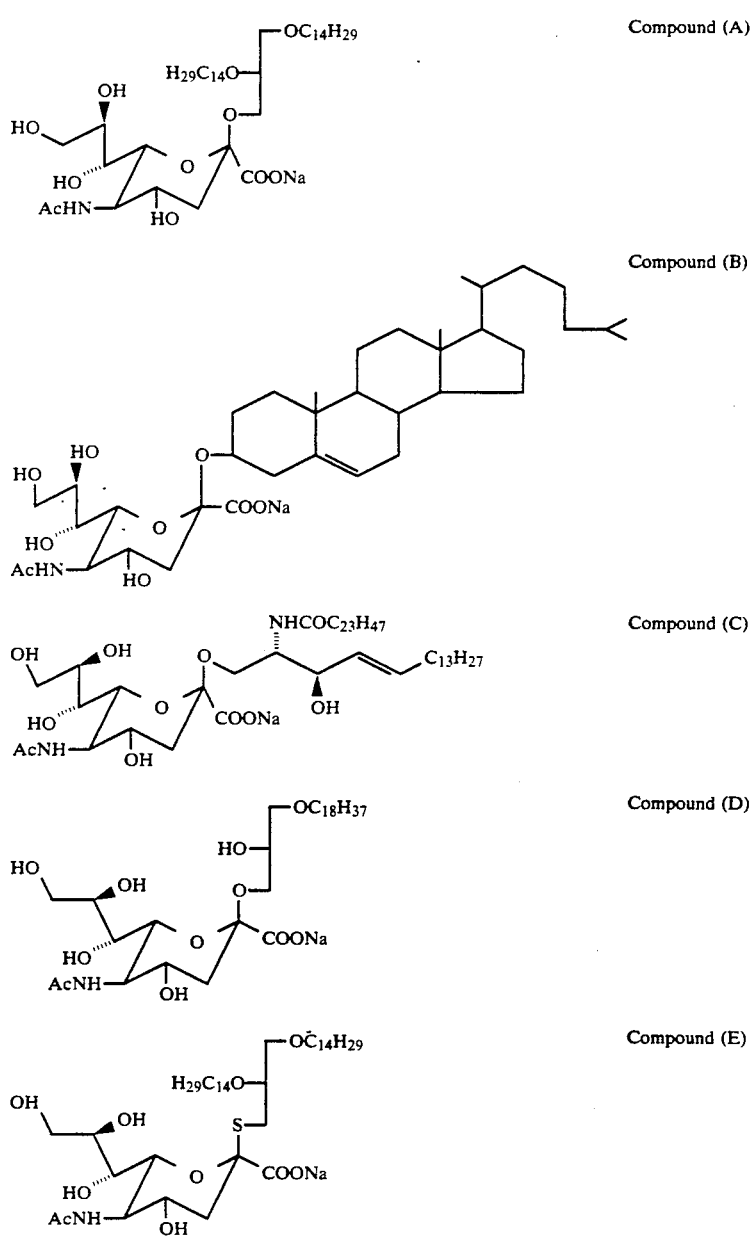

-continued

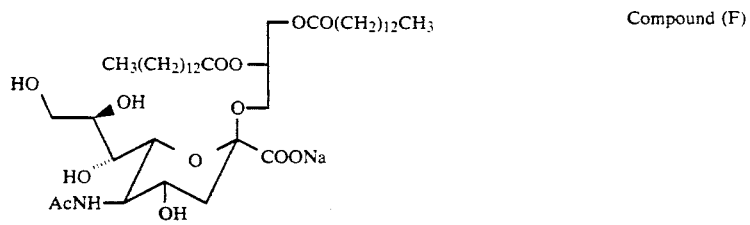

Compound (F)

Specific examples of N-acetylneuraminic acid derivatives in the alpha-arrangement, which are not reactive to the monoclonal antibody of the present invention are as follows:

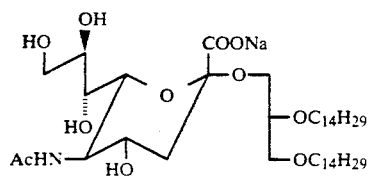

Compound (H)

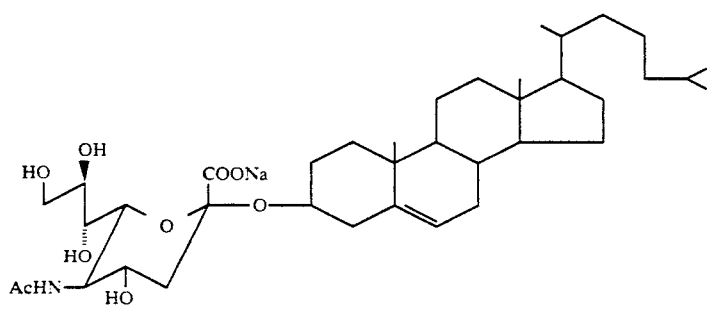

Compound (I)

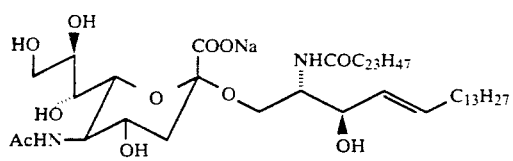

Compound (J)

In the above formulas, Ac represents an acetyl group.

The monoclonal antibody produced by the hybridoma of the present invention recognizes N-acetylneuraminic acid in the beta-arrangement as an epitope or an antigenic determinant and specifically reacts therewith. Therefore, the monoclonal antibody produced by the hybridoma of the present invention would exhibit high specificity to N-acetylneuraminic acid and any derivatives thereof so far as they are in the beta-arrangement.

In the method for producing the hybridoma of the present invention, either of the N-acetylneuraminic acid derivatives such as those listed above is injected into an animal such as a mouse intramuscularly, intravenously, subcutaneously or intraperitonealy to sensitize it and to thereby obtain B cells, in particular spleen B cells or lymphocytes. In this immunization, either incomplete adjuvants or complete adjuvants may be used as an adjuvant, i.e., an agent for immunological enhancement and specific examples thereof are oils, emulsifying agents, killed tubercule bacillus, killed Salmonella and mixture thereof, preferably killed *Salmonella minesota* R 595.

Then, B cells thus obtained are fused with myeloma cells. As the fusing agent used in this cell fusion, there may be mentioned, for instance, polyethylene glycol and HVJ, preferably polyethylene glycol 4,000. In addition, it is preferrable to use HAT medium as the culture medium in order to separate hybridoma cells from the myeloma cells which remains unfused.

Thereafter, the resultant hybridoma cells are subjected to cloning operation such as methylcellulose method, soft agarose method or limiting dilution method to separate a desired single clone.

The antibody titer of the monoclonal antibody producing hybridoma thus obtained can be examined according to the standard method to select hybridoma exhibiting high antibody titer. The hybridoma thus generated is then stored.

The hybridoma of the present invention was deposited on Nov. 11, 1989 with the American Type Culture Collection (ATCC) 12301 Parklawn Drive, Rockville, Md., U.S.A. under the Accession number of HB 9619.

The monoclonal antibody produced by the hybridoma of the present invention can be used in detecting free N-acetylneuraminic acid present in blood or urine of human or animals and/or in determining the amount thereof according to a method such as the competitive RIA method.

Therefore, it is expected to use the monoclonal antibody of the present invention in clinical purposes such as diagnosis and prognosis of a certain kinds of cancers and acute inflammatory diseases. Besides, it may further be used in the basic studies of the functions of N-acetylneuraminic acid in glycolipid-related diseases as well as those of substances which play important roles in living organisms, such as N-acetylneuraminic acid, sialidase and sialyltransferase. It is also possible to purify N-acetylneuraminic acid in the beta-arrangement utilizing the monoclonal antibody thus produced in affinity chromatography.

The present invention will be explained in more detail with reference to the following non-limitative working example.

EXAMPLE

(A) Preparation of Immunogen (1) Synthesis of Compound (A)

There was dissolved, in methanol, 3-0-(methyl-(5-aceta-mido-4,7,8,9-tetra-0-acetyl-3,5-dideoxy-beta-D-glycero-D-galacto-2-nonulopyranosyl)-onate)-1,2-di-0-tetradecyl-Sn-glycerol and the resultant solution was hydrolyzed with 1N sodium hydroxide solution at room temperature. The resulting reaction product was neutralized with Amberlite (trade name of Rhome & Haas Co.) and then was purified by reverse phase chromatography to thus obtain Compound (A) which was subsequently used as an immunogen (see Japanese Patent Unexamined Publication No. 59-164798).

(2) Animals 5 female Balb/c mice of 6 week-old were used for experiments after breeding them for 7 days in an ai-conditioned room.

(3) Preparation of Antigen Solution

Compound (A) (1 mg) and Salmonella minesota R 595(4 mg) treated with acetic acid were dispersed in and mixed with 1 ml of phosphate-buffered saline (PBS (-)) to form an antigen solution.

(4) Culture Medium

Culture Medium: Nissui RPMI 1640 was used as culture medium. To the medium, there were added 100 U/ml of penicillin G potassium, 1 mg titer/ml of streptomycin sulfate, 1 mM of sodium pyruvate and 10% of fetal bovine serum (FBS) prior to use the same.

HAT Medium: 0.0388 g of thymidine and 0.1361 g of hypoxanthine were dissolved in 100 ml of distilled water while heating and the resulting solution (a) was stored at $-20°$ C. as a stock solution having a concentration 100 times higher than the desired one. Likewise, 0.0176 g of aminopterin was dissolved in 100 ml of distilled water by adding a small amount of 1N sodium hydroxide aqueous solution, then this was diluted 10 times with RPMI 1640 culture medium and the resultant solution (b) was stored at $-20°$ C. as a stock solution having 100 times the desired concentration while shielding the light. HAT medium was prepared by adding 1/100 volume each of these two solutions to 10% FBSRPMI 1640 medium immediately before use.

Moreover, HT medium was prepared by simply adding 1/100 volume of the stock solution (a) containing hypoxanthine and thymidine to the same 10% FBSRPMI 1640 medium.

(5) Parent Cells

As the parent cells for cell fusion, there was used myeloma cells (x63-Ag8-6.5.3 cells) which were derived from Balb/c mice. These cells were subjected to subculture in RPMI 1640 medium to which 10% FBS was added while the generation of mutant was inhibited by adding 6-thioguanine to the medium so that the concentration thereof was equal to 3 microgram/ml.

(B) Generation of Hybridoma (1) Method of Immunization

Female Balb/c mice of 6 week-old were immunized by intraperitonealy injecting the following immunogen solution according to the following immunization schedule: initially 5 micrograms; 10 micrograms each at 12 days and 16 days after; and 15 micrograms each at 26 days and 35 days after. Three days after the final immunization, mice were sacrificed to get spleen cells (lymphocytes) and then a suspension of individual spleen cells was prepared from the same.

Immunogen Solution: 1 mg of Compound (A) as immunogen and 4 mg of Salmonella minesota as the adjuvant were mixed in 1ml of phosphate-buffered saline (PBS(-); free from Ca and Mg) and the resultant solution was then appropriately diluted to use as the immunogen solution.

(2) Cell Fusion

Fusion of the spleen cells (lymphocytes) and the mouse myeloma cells as the parent cells was performed according to the method of Kohlor and Millstein. More specifically, $10^8$ spleen lymphocyte obtained 3 days after the final immunization were fused with $10^7$ myeloma cells in the presence of 50% polyethylene glycol (PEG 4000) in a culture medium.

(3) Selection and Beeding of Hybridoma

After the cell fusion, the resultant hybridoma cells were cultured for 15 days in RPMI-1640 medium to which HAT medium and 10% FBS were added.

After the culture for 15 days, the supernatant of the culture medium was examined whether the hybridoma cells produced antibodies specific to Compound (A) or not by enzyme-labeled antibody technique.

(C) Estimation of the Reactivity of the Monoclonal Antibody with N-Acetylneuraminic Acid Derivatives in the Beta-Arrangement (1) Enzyme-labeled Antibody Technique (ELISA Method)

96-well flat-bottomed plate (available from Falcon Co., Ltd.) was pretreated with ethanol before using in experiments. 50 Microliters each of 0.002% ethanol solution of N-acetylneuraminic acid derivative was pippeted into wells of the plate, then the solvent was evaporated off therefrom, 200 microliters each of 0.2% casein PBS(-) solution was introduced into the wells and it was allowed to stand for 2 hours at room temperature. The solution was removed by aspiration, then 50 microliters each of the supernatant of the hybridoma culture medium was added to the wells and the plate was allowed to stand for one hour at room temperature. Likewise, the primary antibody was removed from the plate, then the wells were washed three times by adding 150 microliters of PBS(-) solution and were allowed to stand for 30 minutes at room temperature after the addition of 200 microliters each of 0.2% casein PBS(-) solution. After the removal of the solution, 50 microliters each of secondary antibody which had been diluted to an optimum concentration with 0.2% casein PBS(-) solution was added to the wells and they were allowed to stand for 1.5 hours at room temperature. As in the case of the primary antibody, the wells were washed three times with PBS(-) solution and 100 microliters each of a reaction solution was added to cause reaction in the dark. The reaction solution was prepared by dissolving, into citrate-phosphate buffer (pH 5.0), o-phenylenediamine and hydrogen peroxide so that the final concentrations thereof are 0.4 mg/ml and 0.01% respectively. The reaction was stopped by the addition of 30 microliters each of 8N sulfuric acid solution and thereafter the product was examined by colorimetry at 490 nm. As the secondary antibody, there were used goat anti-mouse IgG, IgM and IgA antibodies labeled with horseradish peroxidase (HRP).

The specificity of the monoclonal antibody, of the present invention, to Compounds (A) to (F) in the beta-arrangement and Compounds (H) to (L) in the alpha-arrangement was examined according to the method explained above and the results obtained were shown in FIGS. 1 to 3 attached hereto.

FIGS. 1 and 2 show the results of the cross reaction between the anti-compound (A) antibody of the present invention and the compounds comprising N-acetylneuraminic acid in the beta arrangement used as an antigen, respectively. As seen from the results plotted on FIGS. 1 and 2, all the compounds comprising N-acetylneuraminic acid in the beta-arrangement are positive in the cross-reaction.

FIG. 3 likewise shows the result of the cross-reaction between the antibody of the present invention and compounds comprising N-acetylneuraminic acid in the alpha-arrangement used as an antigen. As a result, it is found that all the compounds comprising N-acetylneuraminic acid in the alpha-arrangement are negative in the cross-reaction.

Investigation of Competitive Inhibitory effect of Free N-Acetylneuraminic Acid by Enzyme-Labeled Antibody Technique The monoclonal antibody (anti-compound (A) antibody) of the present invention was made to react with Compound (A), as an antigen, coated on a plate in the presence of free N-acetylneuraminic acid to examine the competitive inhibitory effect of free N-acetylneuraminic acid against the binding of the anti-compound (A) antibody and Compound (A) and the results obtained were plotted on FIG. 4.

The results shown in FIG. 4 indicate that the free N-acetylneuraminic acid binds to antigen-binding sites of the anti-compound (A) antibody to inhibit the binding of Compound (A) in proportion to the concentration of the acid. This suggests that the anti-compound (A) antibody of the present invention is an antibody that specifically binds to free N-acetylneuraminic acid.

Investigation of Binding Properties of ($^{14}$C)N-Acetylneuraminic Acid with Anti-compound (A) Antibody The supernatant containing the anti-compound (A) antibodies was stepwise diluted to 1 to 64-fold and was introduced into each well to adhere the antibody thereto. Then, a solution of ($^{14}$C)N-Acetylneuraminic Acid was added to the wells followed by incubating, washing the wells and examining the residual radioactivity of each well. The results obtained are plotted on FIG. 5. It is found, from the results plotted on FIG. 5, that the radioactivity attributable to ($^{14}$C)N-acetylneuraminic acid increases in proportion to the coated amount of the antibody.

The same procedures as above were repeated using glucosamine as an antigen (control), but no binding between the anti-compound (A) antibody and glucosamine was observed. This also clearly indicates that the monoclonal antibody of the present invention specifically reacts with N-acetylneuraminic acid in the beta-arrangement.

What is claimed is;

1. A hybridoma producing a monoclonal antibody which specifically binds free N-acetylneuraminic acid, β-glycosides thereof or β-glycoconjugates thereof, and wherein said monoclonal antibody does not cross-react with an α-glycoside or an α-glycoconjugate of N-acetylneuraminic acid.

2. The hybridoma of claim 1, wherein said hybridoma produces a monoclonal antibody which has all of the identifying characteristics of ATCC HB 9619.

3. The hybridoma of claim 1, wherein said hybridoma is ATCC HB 9619.

4. A monoclonal antibody which specifically binds to N-acetylneuraminic acid, β-glycosides thereof or β-glycoconjugates thereof, wherein said monoclonal antibody does not cross react with an α-glycoside or an α-glycoconjugate of N-acetylneuraminic acid.

5. The monoclonal antibody of claim 4, wherein said monoclonal antibody is of the IgG class.

6. The monoclonal antibody of claim 4, wherein said monoclonal antibody is produced by hybridoma ATCC HB 9619.

* * * * *